United States Patent [19]

Kathawala

[11] 4,020,083
[45] Apr. 26, 1977

[54] 5-(2-AMINOPHENYL)-S-TRIAZOLES

[75] Inventor: Faizulla G. Kathawala, West Orange, N.J.

[73] Assignee: Sandoz, Inc., E. Hanover, N.J.

[22] Filed: July 8, 1975

[21] Appl. No.: 594,125

[52] U.S. Cl. .................... 260/308 R; 424/269; 260/251 Q; 260/256.4 F; 260/256.4 Q
[51] Int. Cl.² ....................................... C07D 249/08
[58] Field of Search ............................... 260/308 R

[56] References Cited

UNITED STATES PATENTS 3,862,137  1/1975  Kathawala .................... 260/308 R

OTHER PUBLICATIONS

Potts et al., Chem. Abstracts, vol. 73, Abstract No. 120582v (1970).
Cipins et al., Chem. Abstracts, vol. 65, Columns 704–705 (1966).

*Primary Examiner*—Alton D. Rollins
*Attorney, Agent, or Firm*—Gerald D. Sharkin; Richard E. Vila; Joseph J. Borovian

[57] ABSTRACT

Anti-inflammatory agents of the formula:

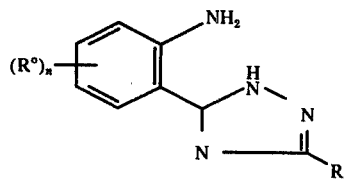

wherein

R° is hydrogen, halo, alkoxy, alkyl, or CF₃ or two adjacent R° together may also form methylenedioxy, R is hydrogen or lower alkyl, and $n$ is 1 or 2.

3 Claims, No Drawings

5-(2-AMINOPHENYL)-S-TRIAZOLES

The compounds 3-(2-aminophenyl)-s-triazole and 3-(2-aminophenyl)-5-methyl-s-triazole have been previously disclosed in the literature by K. T. Potts et al. J.O.C. 35(10) 3448 (1970). In addition, the compound 3-(2-aminophenyl)-5-pyridyl-s-triazole has been described by P. M. Hergenrother, J. Heterocycl. Chem. 1972, 131-136. To my knowledge, no pharmacological activity has been heretofore associated with either of these compounds.

The present invention involves the novel compositions and use of the compounds of formula I:

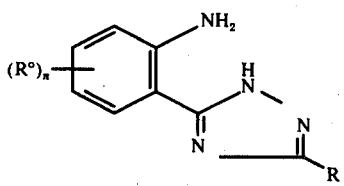

wherein
R° is hydrogen, halo selected from the group consisting of bromo, chloro, and fluoro, alkoxy of 1 to 4 carbon atoms, alkyl of 1 to 4 carbon atoms or $CF_3$ or two adjacent R° together may also form methylenedioxy,
R is hydrogen or alkyl of 1 to 4 carbon atoms, and
n is 1 or 2.

The preferred compound of formula I is that in which R and R° are hydrogen.

The invention further provides the novel compounds of formula Ia:

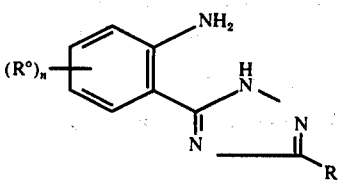

wherein R°, R and n have the same significance as defined above, provided that
i. when n is 1, and one of R° and R signifies hydrogen, the other signifies other than hydrogen,
ii. when n is 1, and R signifies alkyl of 1 to 4 carbon atoms, then R° signifies other than hydrogen, and
iii. when n is 2, and R signifies hydrogen or alkyl of 1 to 4 carbon atoms, then only one R° signifies hydrogen.

The compounds of formula I may be prepared by subjecting a compound of the formula II:

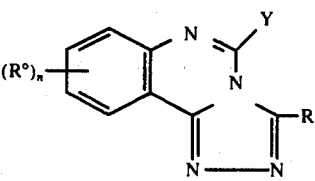

in which R°, R and n are as defined above and Y is hydrogen or a chlorine atom, to the action of a strong inorganic base in the presence of water whereby a combined hydrolysis and rearrangement takes place. Although the reaction temperature is not critical, the process is conveniently carried out at a temperature of at least 40° C. up to 180° C., preferably at reflux temperatures, for a period of suitably between 3 and 60 hours. The reaction is conveniently carried out in an inert liquid medium, which preferably consists essentially of water. The reaction product may be recovered from the reaction mixture by working up by conventional procedures.

The compounds of formula II may be produced by reacting a compound of formula III:

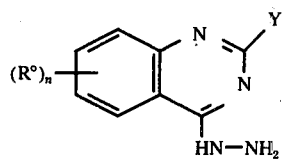

in which R°, n and Y are as defined above with a compound of formula IV:

$$R-C[O-(CH_2)_m-CH_3]_3 \quad \text{IV}$$

in which R is as defined above and m is 0 or 1, under substantially anhydrous conditions, as described in Belgium Pat. No. 792,856.

The compounds of formula III may be produced by reacting a compound of formula V:

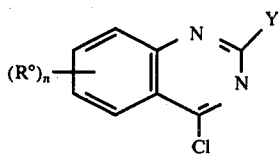

in which R°, n and Y are as defined above, with hydrazine. The process is suitably carried out at a temperature of from 0° to 30° C., preferably 5° to 25° C., and in an inert organic solvent, such as an aromatic solvent, e.g., benzene or toluene, a chlorinated hydrocarbon, e.g., methylene chloride, or a dialkyl amide, e.g., dimethylacetamide. The reaction product may be isolated and purified using conventional techniques.

The compounds of formula V are either known or may be produced in conventional manner from available materials, e.g., by the procedures of Curd et al., J. Chem. Soc. 1948, 1759, Hens et al., J. Med. Chem. 11, 130-136 (1968) and Endicott et al., J.A.C.S., Vol. 68, 1303 (1946).

The compounds of structural formula I are useful because they possess pharmacological activity in animals. In particular, the compounds are useful as anti-inflammatory agents as indicated by the Carrageenan-induced edema test in rats. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 10 milligrams to about 100 milligrams per kilogram of animal body weight, preferably given orally and in divided doses, 2 to 4 times a day, or in sustained release form. For most mammals the total daily dosage is from about 600 milligrams to about 3000 milligrams of the compound, and dosage forms suitable for internal administration comprise from about 150 to 1500 milligrams of the compound in admixture with a solid or liquid pharmaceutically acceptable carrier or diluent.

For above usage, the compounds of structural formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcium phosphate, kaolin, peanut oil, sesame oil and corn oil. The preferred pharmaceutical compositions from the standpoint of preparation and ease of administration are solid compositions, particularly hard-filled capsules and tablets.

Furthermore, the compounds of formula I may be similarly administered in the form of their non-toxic, pharmaceutically acceptable acid addition salts.

Such salts possess the same order of activity as the free base, are readily prepared by reacting the base with an appropriate acid and, accordingly, are included within the scope of the invention. Representative of the acid addition salts are the mineral acid salts, such as the hydrochloride hydrobromide, sulfate, phosphate and the like, and the organic acid salts, such as succinate, benzoate, acetate, p-toluenesulfonate, benzenesulfonate and the like.

Capsules containing the ingredients indicated below may be prepared by conventional techniques and are useful in treating mammals exhibiting inflammatory effects at a dose of one capsule 4 times a day.

| Ingredients | Weight (mg.) |
| --- | --- |
| 5-(2-amino-5-chlorophenyl)-s-triazole | 150 |
| kaolin | 200 |

The following examples are merely illustrative of specific compounds of the invention and the manner in which they may be prepared.

EXAMPLE 1

5-(2-aminophenyl)-s-triazole.

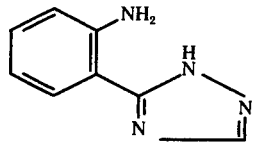

To a flask containing 40 gms. of 5-chloro-1,2,4-triazolo[4,3-c]quinazoline is added 800 ml. of a 10% KOH solution and the resulting mixture heated to reflux. A gentle reflux is maintained overnight after which time the mixture is neutralized to pH 7.0 with cooling and stirring by adding dropwise a 1:1 HCl solution and the resulting precipitate filtered off. The aqueous layer is washed 3 or 4 times with methylene chloride, dried and evaporated in vacuo to dryness. The residue is recrystallized from benzene/ether to obtain 5-(2-aminophenyl)-s-triazole, m.p. 145°–148° C.

A larger quantity of the title compound is obtained by dissolving the precipitate in ethyl acetate, and after filtering off the insoluble material the ethyl acetate layer is dried, evaporated in vacuo to dryness and the residue recrystallized from benzene/ether to obtain 5-(2-aminophenyl)-s-triazole, m.p. 145°–148° C.

EXAMPLE 2

5-(2-amino-4,5-dimethoxyphenyl)-s-triazole.

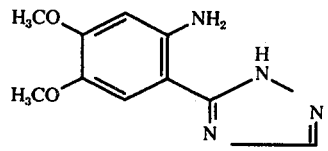

To a flask containing 46 gms. of 5-chloro-8,9-dimethoxy-1,2,4,triazolo[4,3-c]quinazoline is added 1000 ml. of a 10% KOH solution and the resulting mixture heated to reflux. A gentle reflux is maintained overnight after which time the mixture is neutralized to pH 7.0 with cooling and stirring by adding dropwise a 1:1 HCl solution and the resulting precipitate filtered off. The aqueous layer is washed 3 or 4 times with ethyl acetate, dried and evaporated in vacuo to dryness. The residue is recrystallized from ethanol to obtain 5-(2-amino-4,5-dimethoxyphenyl)-s-triazole, m.p. 205°–210° C.

The precipitate is dissolved in ethyl acetate and then air dried. The residue is refluxed with ethanol, filtered off and evaporated in vacuo to dryness. To the resultant residue is poured ether and the precipitate filtered off to obtain 5-(2-amino-4,5-dimethoxyphenyl)-s-triazole, m.p. 205°–210° C.

EXAMPLE 3

5-(2-amino-5-chlorophenyl)-s-triazole.

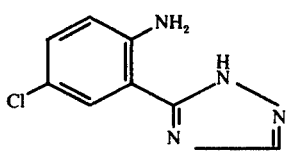

To a flask containing 129.8 gms. of 9-chloro-1,2,4-triazolo[4,3-c]quinazoline is added 2600 ml. of a 10% KOH solution and the resulting mixture heated to reflux. A gentle reflux is maintained overnight after which time the mixture is neutralized to pH 7.0 with cooling and stirring by adding dropwise a 1:1 HCl solution and the resulting precipitate filtered off, washed several times with $H_2O$ and allowed to air dry. The residue was dissolved in methanol and evaporated in vacuo to dryness. The resultant residue is triturated with benzene and the precipitate filtered off to obtain 5-(2-amino-5-chlorophenyl)-s-triazole, m.p. 170°–175° C.

EXAMPLE 4

5-(2-amino-5-chlorophenyl)-3-methyl-s-triazole.

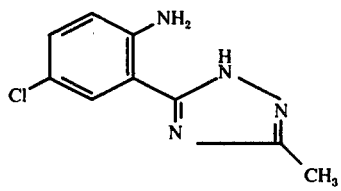

To a flask containing 5 gms. of 9-chloro-3-methyl-1,2,4-triazolo[4,3-c]quinazoline is added 100 ml. of a 10% KOH solution and the resulting mixture heated to reflux. A gentle reflux is maintained for a period of 5½ hours after which time the mixture is neutralized to pH 7.0 with cooling and stirring by adding dropwise a 1:1 HCl solution. The aqueous layer is washed 3 or 4 times with ethyl acetate, washed once with $H_2O$, dried and evaporated in vacuo to dryness. The residue is recrystallized from ether to obtain 5-(2-amino-5-chlorophenyl)-3-methyl-s-triazole, m.p. 190°–195° C.

EXAMPLE 5

Following the procedure of Example 4 and using in place of 9-chloro-3-methyl-1,2,4-triazolo[4,3-c]quinazoline, an equivalent amount of
a. 9-chloro-3-ethyl-1,2,4-triazolo[4,3-c]quinazoline, and
b. 9-chloro-3-propyl-1,2,4-triazolo[4,3-c]quinazoline, there is obtained
a. 5-(2-amino-5-chlorophenyl)-3-ethyl-s-triazole, m.p. 189°–192° C., and
b. 5-(2-amino-5-chlorophenyl)-3-propyl-s-triazole, m.p. 131°–133° C., respectively.

EXAMPLE 6

Following the procedure of Example 2 and using in place of 5-chloro-8,9-dimethoxy-1,2,4-triazolo[4,3-c]quinazoline, an equivalent amount of
a. 5-chloro-8,9-methylenedioxy-1,2,4-triazolo[4,3-c]quinazoline, there is obtained
a. 5-(2-amino-4,5-methylenedioxyphenyl)-s-triazole.

Preparation of
9-chloro-1,2,4-triazolo[4,3-c]quinazoline.

A mixture of 155.7 gms. of 6-chloro-4-hydrazinoquinazoline and 3000 ml. of triethoxy methane is refluxed with stirring for 48 hours, and after filtering off the insoluble material, the filtrate is evaporated in vacuo to dryness and the residue recrystallized from ether to obtain 9-chloro-1,2,4-triazolo[4,3-c]quinazoline, m.p. 179°–182° C.

What is claimed is:

1. A compound of the formula:

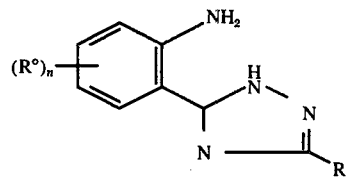

wherein
R° is hydrogen, halo selected from the group consisting of bromo, chloro and fluoro, alkoxy of 1 to 4 carbon atoms, alkyl of 1 to 4 carbon atoms or $CF_3$ or two adjacent R° together form methylenedioxy,
R is hydrogen or alkyl of 1 to 4 carbon atoms, and
n is 1 or 2,
or a pharmaceutically acceptable acid addition salt thereof, provided that
   i. when n is 1, and one of R° and R signifies hydrogen, the other signifies other than hydrogen,
   ii. when n is 1, and R signifies alkyl of 1 to 4 carbon atoms, then R° signifies other than hydrogen, and
   iii. when n is 2, then only one R° signifies hydrogen.

2. A compound of claim 1 having the formula:

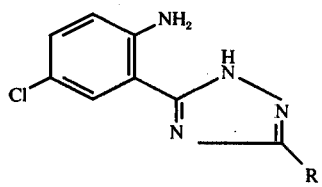

wherein R is as defined in claim 1, or a pharmaceutically acceptable acid addition salt thereof.

3. The compound of claim 2 which is 5-(2-amino-5-chlorophenyl)-s-triazole.

* * * * *